United States Patent
Yamamoto

(10) Patent No.: US 7,015,478 B2
(45) Date of Patent: Mar. 21, 2006

(54) X-RAY IMAGING APPARATUS

(75) Inventor: Osamu Yamamoto, Tochigi (JP)

(73) Assignee: Canon Kabushiki Kaisha, Tokyo (JP)

(*) Notice: Subject to any disclaimer, the term of this patent is extended or adjusted under 35 U.S.C. 154(b) by 237 days.

(21) Appl. No.: 10/715,723

(22) Filed: Nov. 14, 2003

(65) Prior Publication Data

US 2004/0114725 A1   Jun. 17, 2004

(30) Foreign Application Priority Data

Nov. 27, 2002 (JP) .............................. 2002-343406

(51) Int. Cl.
*H01L 27/146* (2006.01)

(52) U.S. Cl. ............................ 250/370.09; 250/370.08; 250/370.1

(58) Field of Classification Search ........... 250/370.08, 250/370.09, 370.1

See application file for complete search history.

(56) References Cited

U.S. PATENT DOCUMENTS

| | | | | |
|---|---|---|---|---|
| 4,092,544 A | * | 5/1978 | Grim | 378/206 |
| 5,493,600 A | * | 2/1996 | Jacobson | 378/207 |
| 5,844,961 A | * | 12/1998 | McEvoy et al. | 378/98.8 |
| 6,533,453 B1 | * | 3/2003 | Heidsieck et al. | 378/189 |

FOREIGN PATENT DOCUMENTS

| | | |
|---|---|---|
| JP | 08-116043 | 5/1996 |
| JP | 8-289883 | 11/1996 |
| JP | 2002-082172 | 3/2002 |

* cited by examiner

*Primary Examiner*—David Porta
*Assistant Examiner*—Christopher Webb
(74) *Attorney, Agent, or Firm*—Morgan & Finnegan, LLP

(57) ABSTRACT

An electronic cassette accommodating a sensor for converting radiation into an electric signal. A cable with a specific length is connected to a side surface of the electronic cassette. A connector that is connectable with a wireless communication unit or an external power source is provided at an end of the cable.

2 Claims, 5 Drawing Sheets

X-RAY IMAGING APPARATUS

BACKGROUND OF THE INVENTION

1. Filed of the Invention

The present invention relates to an X-ray imaging apparatus used for medical diagnosis and particularly relates to a portable imaging apparatus having an area sensor serving as an X-ray receiving medium in which multiple photoelectric conversion elements are two-dimensionally arranged on the same plane.

2. Related Background Art

It is a widely used method, in the field of nondestructive inspection for industrial purpose and in the field of medical diagnosis, to obtain a radiation image of an object to be imaged by irradiating the object to be imaged with radiation and detecting the intensity distribution of the radiation that has been transmitted through the object to be imaged. Specifically, a general method of obtaining a radiation image of an object includes the steps of preparing a combination of a silver film and a so-called fluorescent screen (or an intensifying screen) that emits fluorescent light upon receiving radiation, irradiating an object to be imaged with X-rays, converting the transmitted radiation into visible light by means of the fluorescent screen to form an latent image on the silver film, and then chemically processing the silver film to obtain a visible image. The radiation image obtained by this method is an analogue photograph, which is to be used for diagnosis, inspection or other purposes.

On the other hand, recently there has been developed technology for obtaining a digital image using a two dimensional array sensor as image receiving means in which pixels composed of micro photoelectric conversion elements or switching elements are arranged in a lattice-like pattern. Such an imaging apparatus can display obtained image data immediately, so that it may be called a direct X-ray digital imaging apparatus. Advantages of the X-ray digital imaging apparatus over conventional analogue photographing technologies are elimination of the need for films, enlargement of obtained image information realized by image processing and capability of constructing a database etc.

Digital image data obtained from an X-ray digital imaging apparatus is transferred to a system control unit or a storage server etc. via wired or wireless data transmission.

X-ray imaging apparatuses for forming still images for medical use are categorized, based on the scheme of imaging of a patient as an object to be imaged, into stationary type apparatuses and portable type apparatuses. An example of the stationary type apparatus is provided with a table and an imaging portion containing a film or a photoelectric conversion apparatus and it radiates X-rays to a patient from above to obtain an abdominal image of the patient. The portable type apparatus uses a lightweight box called a cassette in which a film is accommodated. The portable type apparatus is used in the case that the condition of a patient is too bad to be brought from a bed in a ward to a table in an X-ray room in which a stationary type apparatus is installed or in the case that a special imaging method that cannot be put into practice by a stationary apparatus is required. In the former case, an operator brings a cassette and an portable X-ray imaging apparatus to the patient's ward, so that the operator performs imaging in the ward.

In view of portability and operationality, it is desirable that the portable apparatus be made as compact and lightweight as possible. However, in the case that the X-ray digital imaging apparatus is to be constructed as a portable apparatus (which will be referred to as an electronic cassette hereinafter), the apparatus includes, in order to output an X-ray transmission image of a patient as a digital image data, many components such as a two-dimensional array sensor for receiving an X-ray image, a drive circuit for driving the sensor in accordance with a control signal sent from an X-ray generating apparatus, an amplifier for selecting matrices within the sensor by means of the drive circuit to amplify the data of each matrix, an A/D conversion circuit for converting the output of the amplifier into digital data and a circuit for serializing the image data that has been sequentially digitized by the A/D converting circuit and the drive circuit. Therefore, it is difficult to make the electronic cassette compact and lightweight as compared to the film cassette. In addition, in the case that wireless data transmission is adopted, a memory for temporally storing data and a battery for supplying power to the electronic cassette are further required. This leads to an additional increase in the size and weight of the electronic cassette. In the case that the number of times of imaging with the electronic cassette is small, the size of the memory and the battery can be made small, so that an increase in the weight may be small. However, in order to eliminate the risk of overflow of memory during imaging and the risk of running out of battery, and since the transfer rate of wireless connection is lower than that of wired connection, the wired connection should also be taken into consideration. On the other hand, in the case that the number of times of imaging is large, it is desirable that the connection scheme be specialized to the wired (or cable) connection, the circuitry for wired data transferring be contained in the electronic cassette, which should be made as compact and lightweight as possible, and a cable for the wired connection be connected to the electronic cassette only at the time of imaging and data transmission.

FIG. 6 shows an example of a state of use of an electronic cassette that can be connected with a cable. The patient P shown in FIG. 6 is a patient lying on a bed 48 in a ward. The condition of the patient P is so bad that he or she cannot be brought to an X-ray room in which a stationary X-ray imaging apparatus is installed. Therefore, an operator (not shown) brings an electronic cassette 49 and an portable X-ray generating apparatus 34 to the patient's ward so as to perform imaging. The electronic cassette 49 can be detachably connected with a cable 5, through which data is transmitted and electric power is supplied, via a connector 50. The cable 5 is connected to a system control portion 27 and a power source portion 28 of the electronic cassette 49. The system control portion 27 controls the operations of the overall system such as control commands to the electronic cassette 49, receiving of digital image data and communication with the portable X-ray generating apparatus 34 etc. The power source portion 28 transforms an AC voltage of a commercial power source into a predetermined DC voltage for the electronic cassette 49 to supply it to the electronic cassette 49. The system control portion 27 and the power source portion 28 are accommodated in the same case having wheels (not shown) with a view to improving portability. The cable 5 is a composite cable including a signal line between the electronic cassette 49 and the control portion 27 and a power supply line between the electronic cassette 49 and the power source portion 28. Though two wires for a power system and a signal system respectively are included in the same cable, the wires are separated into a signal line and a power line at the cable end facing the power source portion 28 and the cable end facing the electronic cassette 49.

In one example of imaging, as a first step of the imaging process, the operator inserts the electronic cassette 49 that is not connected with the cable 5 between the patient P and the bed 48 at the position as shown in FIG. 7. The insertion is normally performed from a side of the patient as shown in FIG. 6. The reason why the electronic cassette 49 is inserted under the unconnected state is to eliminate the troublesome operation of determining the position of the electronic cassette while paying attention to the cable so that the cable will not fall into the imaging area. The electronic cassette 49 is positioned at the area in which an image of the patient to be obtained. After the electronic cassette 49 is positioned, the cable 5 is connected to the connector 50. Then, the operator performs, via an interface 30 of the system control portion 27 various setting such as setting of imaging conditions necessary for imaging (the X-ray tube voltage, the tube current and the X-ray irradiation time etc), imaging timing, image processing conditions, patient's ID, method of processing input images. The interface 30 includes a touch panel, a mouse, a keyboard or a foot switch etc. The system control portion 27 drives the portable X-ray generating apparatus 34 and the electronic cassette 49 based on the set imaging conditions. The portable X-ray generating apparatus 34 includes an X-ray tube 35 and an X-ray stop 37. The X-ray tube 35 is driven by a power source 36 for generating a high voltage controlled by the system control portion 27 to radiate an X-ray beam. The X-ray stop 37 shapes the X-ray beam in accordance with a change in the imaging area so that unnecessary X-ray irradiation is not performed. The X-ray beam is directed to the patient P lying on the bed 48. The electronic cassette 49 is irradiated with the X-ray beam that has been transmitted through the patient P. The electronic cassette 49 accommodates a scintillator for converting X-rays into visible light and a photo detector array as an X-ray receiving medium in which thin film transistors (TFT) are arranged similar to those disclosed in Japanese Patent Application Laid-Open No. 08-116043. An X-ray image of the patient that has been irradiated with the X-ray beam is converted into visible light by the scintillator in the interior of the electronic cassette 49 and the resultant visible light is subjected to photoelectric conversion in the photo detector array. After that, amplification processing and A/D conversion processing are performed, so that serialized digital image data is sent from the electronic cassette to the system control portion 27 via the signal line of the cable 5. The system control portion 27 performs switching of data to be displayed on a monitor 31, real time correction and spatial filtering of the digital image data, tone processing, DR compression etc. The processed image is displayed on the monitor 31. The processed digital data is stored in a memory apparatus 38 at the same time with the real time image processing. Preferably, the memory apparatus 38 is a data storage apparatus that meets large capacity, high speed and high reliability requirements. For example, hard disk arrays such as RAID are preferable. After the data is stored, the cable 5 is disconnected from the connector 50 and the electronic cassette 49 is drawn out from between the patient P and the bed 48. Thus the imaging process is terminated.

The system control portion 27 is provided with a LAN board (not shown), through which the system control portion 27 can be connected to a LAN. A file server in which image data is to be filed, an image printer for outputting an image on a film and an image processing terminal for facilitating complex image processing and diagnosis etc. are connected to the LAN. The system control portion 27 outputs digital image data in accordance with a predetermined protocol (for example, DICOM). After the imaging of the patient P is finished, the operator brings the system to a site at which a port for allowing connection to the LAN is available so as to perform an output operation. The port may be provided in the ward in which the patient P stays so that the output operation may be performed immediately after the completion of imaging.

(Reference: Japanese Patent Application Laid-Open No. 2002-82172)

However, the above-described structure of the electronic cassette suffers from the following problems.

FIG. 8 shows a case in which a connector provided on an electronic cassette 51 having the structure same as the above-described electronic cassette 49 is present between a patient P and a bed 48. This situation can occur in the case that the outer size of the electronic cassette 51 is smaller relative to the patient P. This is the case for example when the width of the body of the patient P is larger than the standard width or when the outer size of the electronic cassette is equivalent to the 12×10 inches size or 10×8 inches size in the case of the film cassette. When the operator places the electronic cassette in position, the cable 5 has not been connected yet. Then, it is necessary for the operator either to connect the cable while raising up the patient P or to once draw out the electronic cassette 51 and move the electronic cassette to a position which allows connection with the cable 5 so as to connect the cable. In any case, it is necessary to change the position relative to the patient P. In addition, there is a risk that the position of the electronic cassette can be displaced and the part to be imaged can deviate from the imaging area. In that case, imaging must be performed again. In addition, since the portable cassette is used not only in the above-described imaging manner but also in various positions for a patient who cannot move, it is necessary for the operator to perform imaging while always paying attention to the position of the connector of the electronic cassette. This is troublesome for the operator.

SUMMARY OF THE INVENTION

Under the above-described situations, an object of the present invention is to provide an X-ray imaging apparatus that has an improved cable connectability.

According to one aspect of the present invention, there is provided an X-ray imaging apparatus comprising:
 a sensor for converting radiation into an electric signal;
 an electronic cassette for accommodating the sensor;
 a first cable connected to a side surface of the electronic cassette; and
 a first connector provided at an end of the first cable.

According to another aspect of the present invention, there is provided an X-ray imaging apparatus comprising:
 a sensor for converting radiation into an electric signal;
 an electronic cassette for accommodating the sensor;
 a first cable connected to a side surface of the electronic cassette; and
 a first connector provided at an end of the first cable;
 a second connector to be connected to the first connector;
 a second cable connected to the second connector; and
 an external apparatus connected to the second cable for transmitting/receiving an electric signal to/from the electronic cassette via the first and second cables and/or supplying electric power to the cassette.

Other features and advantages of the present invention will be apparent from the following descriptions taken in conjunction with the accompanying drawings, throughout which like reference characters designate the same or similar parts.

BRIEF DESCRIPTION OF THE DRAWINGS

The accompanying drawings, which are incorporated in and constitute a part of the specification, illustrate embodiments of the invention and, together with the description, serve to explain the principle of the invention.

DETAILED DESCRIPTION OF THE PREFERRED EMBODIMENTS

Figure 1A:
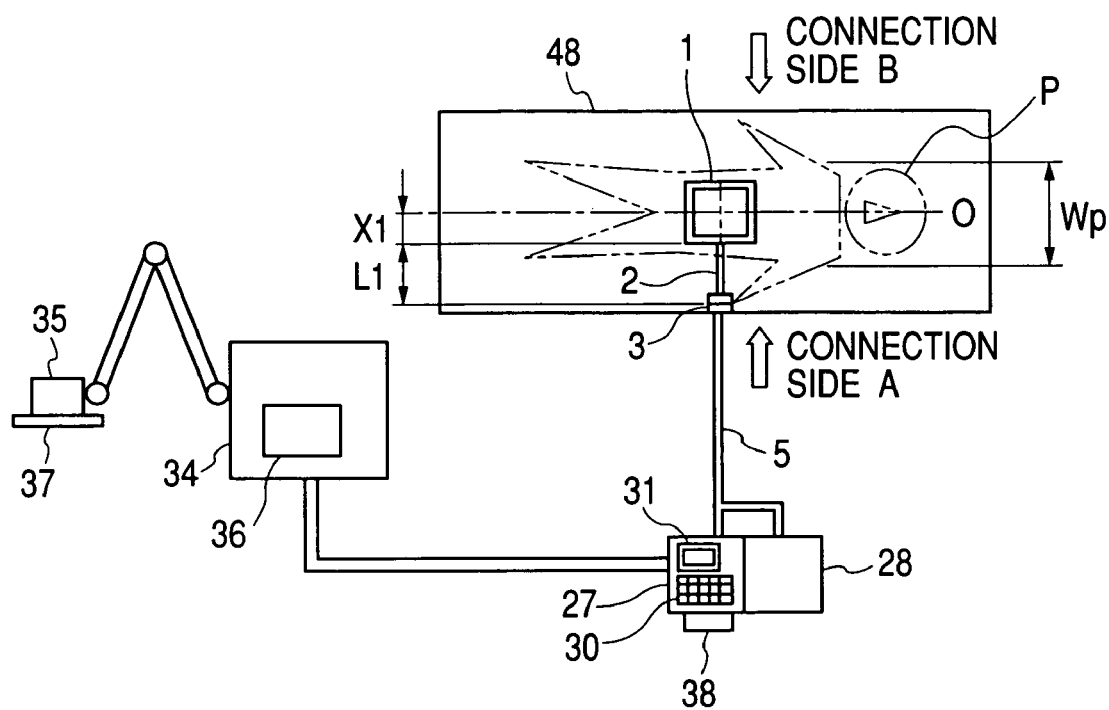
FIGS. 1A and 1B show the structure of an X-ray imaging apparatus.

Preferred embodiments of the present invention will be described in detail with reference to the accompanying drawings.

The present invention as defined by the claims will be described based on embodiments illustrated in the drawings.

Figure 1B:
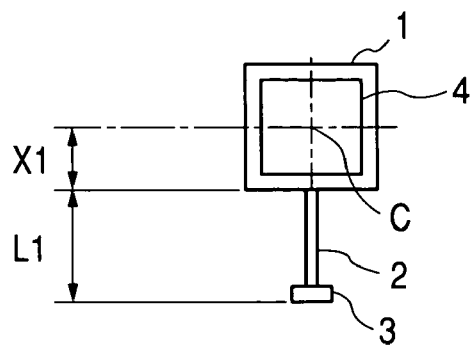

FIGS. 1A and 1B are diagrams showing the structure of a first embodiment. Parts equivalent to those in the previously mentioned drawings will be designated by the same reference characters.

Figure 6:
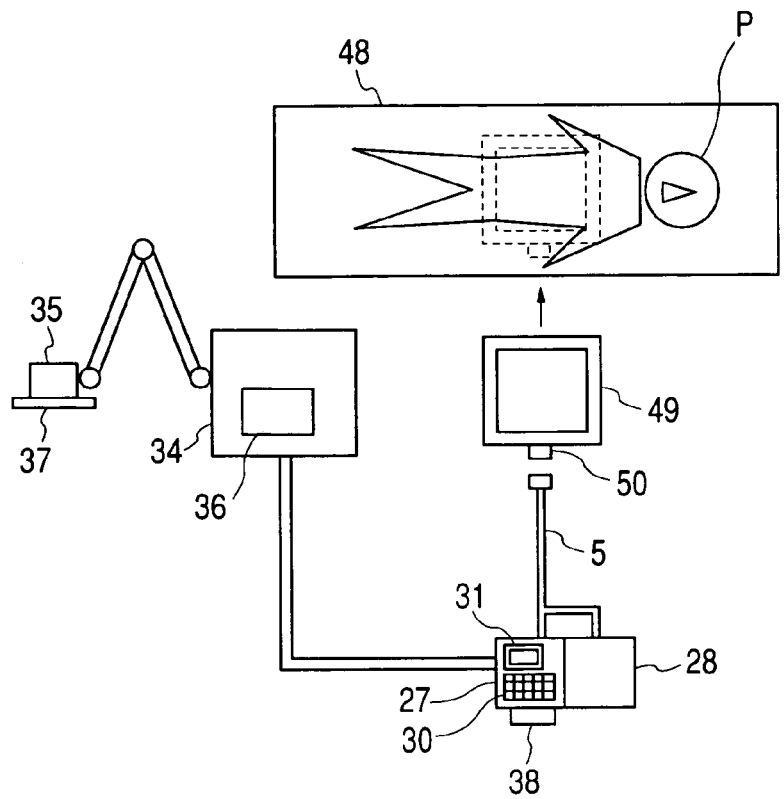
FIG. 6 shows the structure of an electronic cassette according to a prior art.
Figure 7:
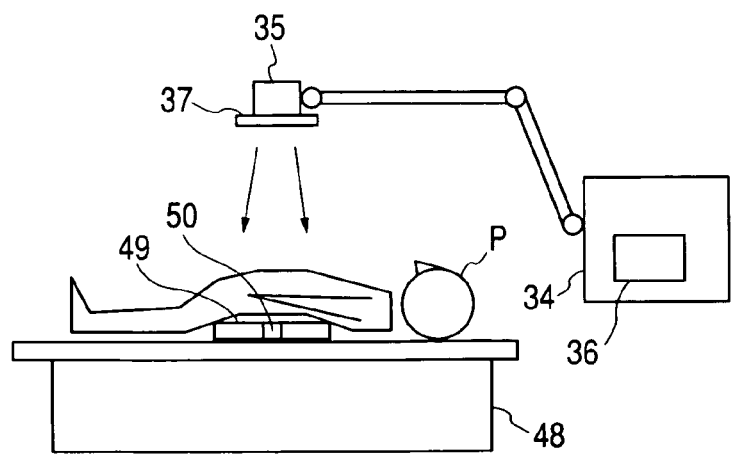
FIG. 7 shows the structure of an electronic cassette according to a prior art.
Figure 8:
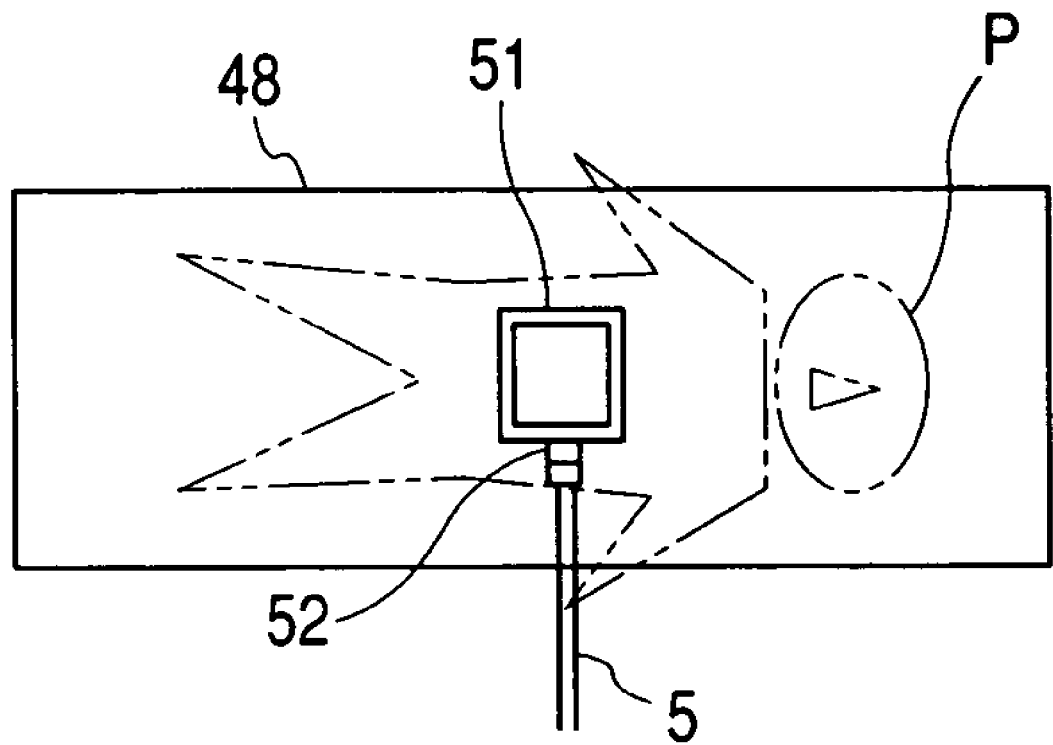
FIG. 8 shows the structure of an electronic cassette according to a prior art.

What is different in this embodiment from the electronic cassette 49 shown in FIG. 6 is that a cable 2 is connected to the case of an electronic cassette 1 and a connector 3 is provided at the end of the cable 2. In FIG. 1B, L1 represents the distance from the side surface of the electronic cassette 1 to which the cable 2 is connected to the end of the cable 3, and X1 represents the distance from the center C of the imaging area 4 of the electronic cassette 1 to the aforementioned side surface of the electronic cassette 1. The electronic cassette 1 has a connection port for the cable 2 provided on the aforementioned side surface. In FIG. 1A, Wp represents the shoulder width or the maximum body width defined by Japanese Industrial Standards (JIS) Z8500 (directed to measurement of human body), and line O represents the center line of the body axis.

In the case shown in FIG. 1A, the center C of the imaging area 4 of the electronic cassette 1 is positioned on the center line of the body axis O and a cable 5 is connected to the connector 3. In this state, since the electronic cassette 1 is placed between the patient P and the bed 48, it is difficult for an operator to visually observe the electronic cassette 1. However, in the electronic cassette 1, since the connector 3 is spaced apart from the body of the electronic cassette 1 on the connection side A via the cable 2, the operator can connect it with the cable 5 as long as the connecter 3 projects outside the area of the body of the patient P. The cable 5 is used for power supply to the electronic cassette 1 and signal transmission after it is connected, as has been described in connection with FIG. 6.

If the distance L1 is set in the range that satisfies the formula $L1 \geq Wp/2 - X1$, the connector 3 will be either at a position in the vicinity of the side face of the body of the patient P facing the connection side A at least or at a position in which the connector 3 projects outside the area of the body of the patient P, and therefore the operator can connect the connector 3 and the cable 5 shown in FIG. 1A easily. By way of example, it is assumed here that the size of the electronic cassette is JL10×12 size defined by Japanese Industrial Standards (JIS) Z4905 and the Wp is 45 cm, which is approximately the average shoulder width of Japanese adult males. The cable connection side is a long side of the electronic cassette 1. In the case that the aforementioned long side is used as the connection side, X1 is equal to 281.5/2 mm. Therefore, if L1 is larger than 84.25 mm, the cable connecting operation will be easily performed. If Wp in the above formula is set to the maximum body width, the cable will further projects outside the area of the body. This makes the connecting operation easier.

Since the distance L1 is a function of X1 mainly, when the size of the electronic cassette is increased, L1 becomes relatively small. While in the situation shown in FIG. 1A, the center C of the imaging area 4 is located on the center line of the body axis O, in the case that the electronic cassette 1 is to be placed in such a way that the center C of the imaging area 4 is at a position above (in the plane of FIG. 1A) the center line of the body axis O, the operator can connect the cable in a manner similar to the above by changing, before placing the electronic cassette 1, the orientation of the connection side surface of the electronic cassette 1 in such a way that the connector 3 projects toward the connection side B.

Figure 2:
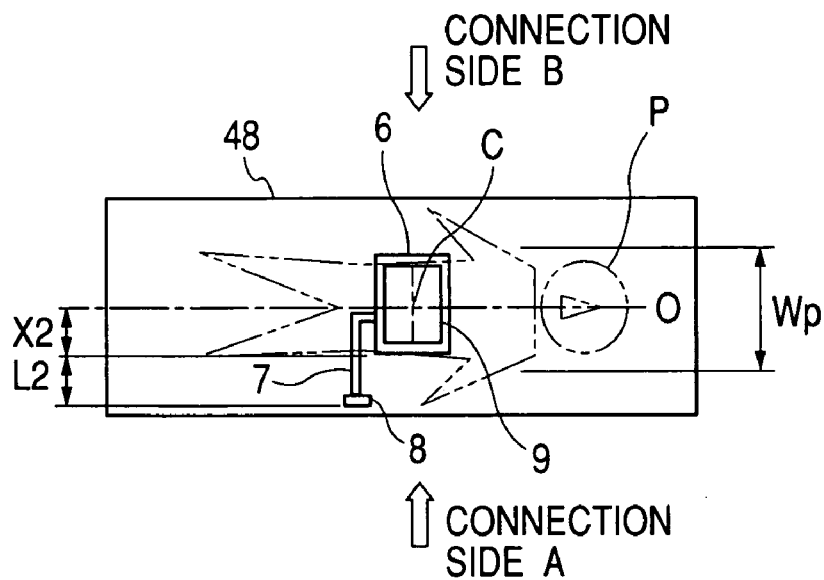
FIG. 2 shows the structure of a rectangular electronic cassette and a cable

FIG. 2 is a diagram showing the structure of a second embodiment of the present invention. In FIG. 2, the parts same as those in the previously mentioned drawings are designated by the same reference characters.

What is different in this embodiment from the electronic cassette 1 shown in FIGS. 1A and 1B is that the electronic cassette has a substantially rectangular shape, the connection port for a cable 7 is provided on a long side of it, and a connector 8 is provided at the end of the cable 7. The imaging area 9 also has a substantially rectangular shape. In the situation shown in FIG. 2, the electronic cassette 6 is disposed in such a way that its long side is perpendicular to the center line of the body axis O of the patient P. Therefore, the connection port for the cable 7 can hardly be visually observed, since it is beneath the body of the patient P. However, letting L2 be the distance from the side surface of the electronic cassette 6 to which the cable 7 is connected to the end of the connector 8, and letting X2 be the distance from the center C of the imaging area 9 of the electronic cassette 6 to the above-mentioned side surface of the electronic cassette 6, when the distance L2 satisfies the formula $L2 \geq Wp/2 - X2$, the connector 8 will be either at a position in the vicinity of the side face of the body of the patient P facing the connection side A at least or at a position in which the connector 8 projects outside the area of the body of the patient P, and therefore the operator can connect the connector 8 and the cable 5 shown in FIG. 1A easily.

As per the above, since L1 and L2 do not represent the cable length but the distance from the side surface of the electronic cassette to the connector, they do not depend on the position of the connection port for the cable.

Figure 3:
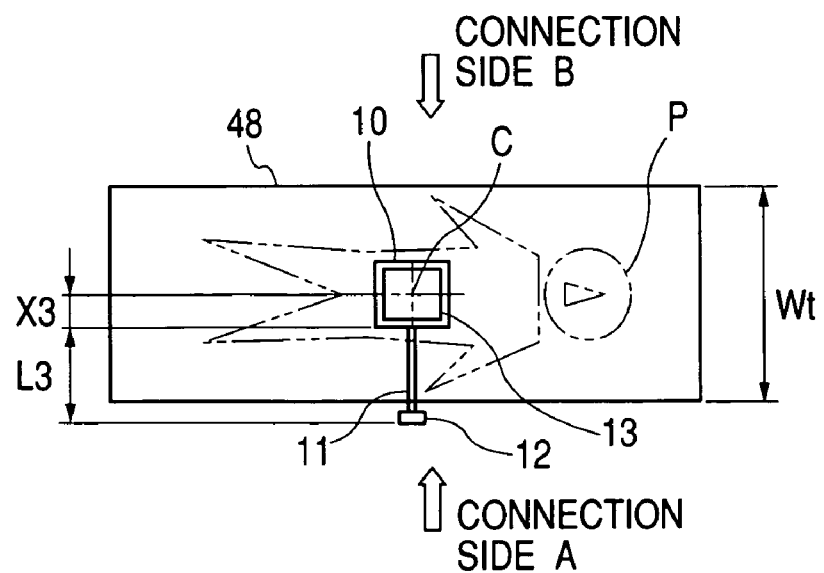
FIG. 3 shows the structure of an electronic cassette and a cable.

FIG. 3 is a diagram showing the structure of a third embodiment of the present invention. In FIG. 3, the parts same as those in the previously mentioned drawings are designated by the same reference characters.

What is different in this embodiment from the electronic cassette 49 shown in FIG. 6 is that a cable 11 is connected to the case of an electronic cassette 10 and a connector 12 is provided at the end of the cable 11. In FIG. 3, L3 represents the distance from the side surface of the electronic cassette 10 facing the connection side A to the end of the cable 12, and X3 represents the distance from the center C of the imaging area 13 of the electronic cassette 10 to the aforementioned side surface of the electronic cassette 10. The electronic cassette 10 has a connection port for the cable 11 provided on the aforementioned side surface. In addition, Wt represents the width of the bed 48. Specifically, the width Wt represents the width of the bed 48 in the direction perpendicular to the body axis of the patient P.

In the case shown in FIG. 3, it is difficult for the operator to visually observe the electronic cassette 10, since the electronic cassette is placed between the patient P and the bed 48.

If the distance L3 is set in the range that satisfies the formula L3≧Wt/2−X3, the connector 12 will be either at a position in the vicinity of the side face of the body of the patient P facing the connection side A at least or at a position in which the connector 12 projects outside the area of the body of the patient P even if the center C of the imaging area 13 of the electronic cassette 10 is positioned on the center line with respect to the width of the bed 48, in other words if the electronic cassette 10 is positioned at the position farthest from the both sides of the bed 48. Therefore the operator can connect the connector 12 and the cable 5 shown in FIG. 1A easily. After connected, the cable 5 is used for power supply to the electronic cassette 10 and signal transmission, as has been described in connection with FIG. 6. By way of example, it is assumed here that the size of the electronic cassette is JL10×12 size defined by Japanese Industrial Standards (JIS) Z4905 and Wt is 90 cm. The cable connection side is a long side of the electronic cassette 1. In the case that the aforementioned long side is used as the connection side, X3 is equal to 281.5/2 mm. Therefore, if L1 is larger than 309.25 mm, the cable connecting operation will be easily performed.

In the case that the electronic cassette 10 is to be placed at a position in which the center C is displaced from the center line of the bed 48 toward the connection side B, the operator may change, before placing the electronic cassette 10, the orientation of the connection side surface of the electronic cassette 10 in such a way that the connector 12 projects toward the connection side B in a manner similar to the embodiment shown in FIGS. 1A and 1B. While in the present embodiment the formulation is made with reference to the width of the bed, it may be made with reference to the width of a top plate of imaging table used in X-ray imaging room directly.

Furthermore, in the arrangement shown in FIG. 3, the connection port for the cable 11 is provided on the connection side surface of the electronic cassette 10. However, since L3 does not represent the cable length but the distance from the side surface of the electronic cassette to the connector, it does not depend on the position of the connection port for the cable.

Figure 4:
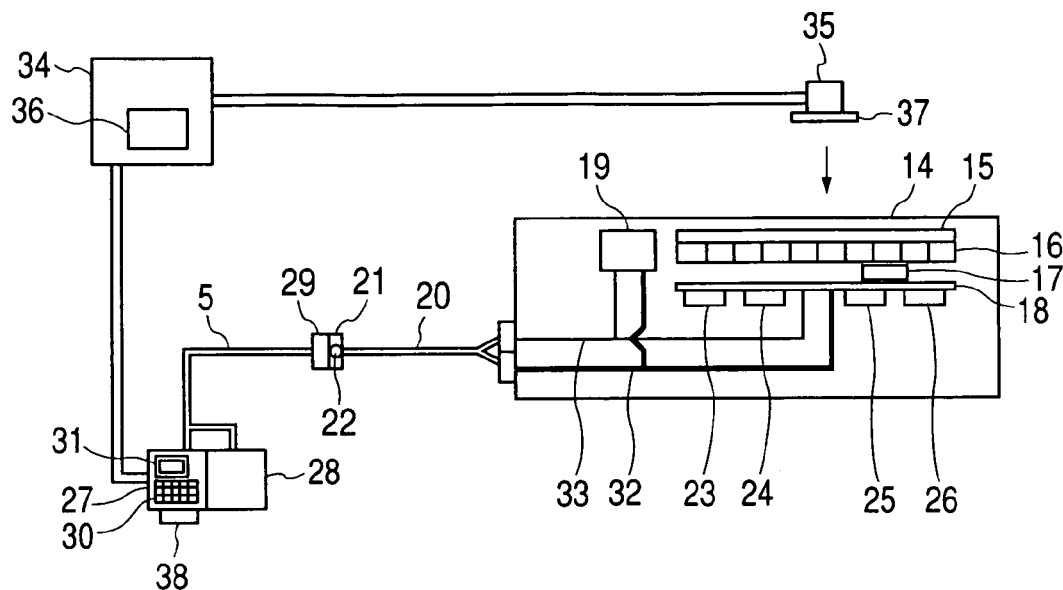
FIG. 4 shows a internal structure of an electronic cassette.

FIG. 4 is a diagram showing the structure of a fourth embodiment, in which the interior of an electronic cassette 14 is illustrated. In FIG. 4, the parts same as those in the previously mentioned drawings are designated by the same reference characters.

The electronic cassette 14 is mainly composed of a scintillator 15, a photo detector array 16, an X-ray exposure dose monitor 17, an electric circuit board 18, a connection controller 19, a cable 20, a connector 21 and an indicator 22. On the electric circuit board 18, there is mounted a drive circuit 23, an amplifier 24, an A/D conversion circuit 25 and a serializing circuit 26. In addition, cable wiring for signal transmission and power transmission between those components is also provided. On the other hand, a cable 5 for connecting a system control portion 27 and a power source portion 28 to the electronic cassette 14 is provided with a connector 29 to be connected with the connector 21.

Next, operations of the electronic cassette 14 and the system control portion under different connection states will be described.

First, under the state in which the connector 21 of the electronic cassette 14 side is not connected with the connector 29 of the system control portion 27 and the power source portion 28 side, the components in the electronic cassette 14 do not operate, since power is not supplied to the electronic cassette 14. In addition, the indicator 22 provided in the connector is not supplied with power, and therefore it does not emit light. The system control portion 27 detects that the connection has not been established, based on absence of communication with the connection control portion 19 and sends a command to a monitor 31 for displaying input information from interface 30 and image data, to cause the monitor 31 to display a content indicating the disconnected state.

When the operator connects the connector 21 on the electronic cassette 14 side and the connector 29 on the system control portion 27 and the power source portion 28 side after placing the electronic cassette 14 in position, electric power is supplied from the power source portion 28 to the connection control portion 19 via the cable 20 and the power supply cable 32. Upon receiving power supply, the connection control portion 19 recognize the connection. Once the connector 5 and the connector 20 are connected, power is also supplied to the indicator 22. Then the connection control portion 19 causes the indicator to emit blue or bluish light to indicate that the electronic cassette 14 is out of imaging operation and detachment is allowed, until the connection control portion 19 receives a command signal for imaging from the system control portion 27. Under this state, the power source portion 28 only supply power required for operations of the components of the connection control portion 19 and the indicator 22. In other words, power has not been supplied to each component of the sensor via the power supply cable 32 yet. The connection control portion 19 informs the system control portion 27 of the fact that the connection with the electronic cassette 14 has been established via the signal cable 33. Based on this information, the system control portion 27 sends a command to the monitor 31 to cause it to display a content indicating that the electronic cassette 14 is in a detachable state.

Next, the operator enters through the interface 30 an imaging start command for the system control portion 27 in order to perform the imaging operation. Upon receiving the command, the system control portion 27 transmits a start command to the connection control portion 19. In response to the start command, the connection control portion 19 transmits a command to the indicator 22 to cause the indicator to emit red or redish light indicating that detachment is not allowed.

At the same time, the system control portion 27 sends a command to the monitor 31 to cause it to display a content indicating that detachment is not allowed.

After the above-described operations are completed, the system control portion 27 commands the power source portion 28 so that electric power required for driving of the components of the sensor is supplied from the power source portion 28 via the power supply cable 32. At the same time, the system control portion 27 transmits an imaging command signal to the electric circuit board 18 via the signal cable 33. In addition, the system control portion 27 drives the X-ray tube 35 of a portable X-ray generating apparatus 34 by means of a high voltage generating power source 36, drives an X-ray stop 37 to set an irradiation field, and causes an X-ray beam to be radiated. The drive circuit 23 on the electric circuit board 18 detects an X-ray exposure termination signal from the X-ray exposure dose monitor 17, high voltage power application from the high voltage generating power source 36 or an X-ray tube current signal to drive the TFT switches so as to read out electric charges. In the scintillator 15, the base material of the phosphor is exited by high energy X-rays and fluorescence within the visible light range is generated by recombination energy released upon recombination. The fluorescence is either based on the base material itself such as CaWO4 or CdWO4 or a luminescence center material such as CSI:Ti or ZnS:Ag activated in the base material.

The photo detector array 16 is provided in close contact with the scintillator 15. The photo detector array 16 converts light generated in the scintillator 15 into an electric signal. The X-ray exposure dose monitor 17 is provided for monitoring the X-ray exposure dose. The X-ray exposure dose monitor 17 directly detect X-rays using a light receiving element made of crystal silicon. Visible light transmitted through the photo detector array 16 is detected by an amorphous silicon light receiving element laminated on the backside of the substrate of the photo detector array 16. The detected information is transmitted to the system control portion 27, so that the system control portion 27 drives the high voltage generating power source 36 to stop or adjust the X-rays based on that information. The drive circuit 23 drives the photo detector array 16 under a control of the system control portion 27 to read out a signal from each pixel. Matrices in the sensor are subjected to selection by the drive circuit 23 and digital image data is obtained by processing data of each matrix by the amplifier 24 for amplifying the data, the A/D conversion circuit 25 for converting the output of the amplifier into digital data and the serializing circuit 26 for serializing the image data that has been sequentially digitized by the A/D conversion circuit 25 and the drive circuit 23. The obtained digital image data is transmitted to the system control circuit 27 and stored in a recording apparatus 38.

After the transmission of the digital image data to the system control portion 27, the power source portion 28 stops power supply to the components of the sensor based on a command by the system control portion 27.

After the digital image data has been stored in the recording apparatus 38 and the system control portion has sent the stop command to the power source portion 28, the system control portion 27 transmits an imaging termination command to the connection control portion 19 via the signal cable 33. Upon receiving the command, the connection control portion 19 transmits a command to the indicator 22 to cause it to emit bluish light so as to indicate that detachment of the electronic cassette 14 is allowed. Under this state, the operator may disconnect the connector 21 and the connector 29. The system control portion 27 sends a command to the monitor 31 to cause it to display a content indicating that detachment of the electronic cassette 14 is allowed.

After checking the indicator or the display on the monitor 31, the operator disconnects the connector 21 and the connector 29 to detach the electronic cassette 14. Thus, the imaging operation on the patient P is finished. The filing of the stored digital image data is performed in the manner same as that described in connection with the prior art.

As per the above, with the provision of the indicator, the operator can recognize the operation state of the electronic cassette. Consequently, it is possible to avoid damage on the sensor circuit that can be caused by instantaneous power shutdown due to abrupt disconnection of the connectors while the power is supplied to the sensor. In addition, since the indicator is provided on the connector to be connected, the operator can easily check the indicator as described in the previous embodiment.

Figure 5:
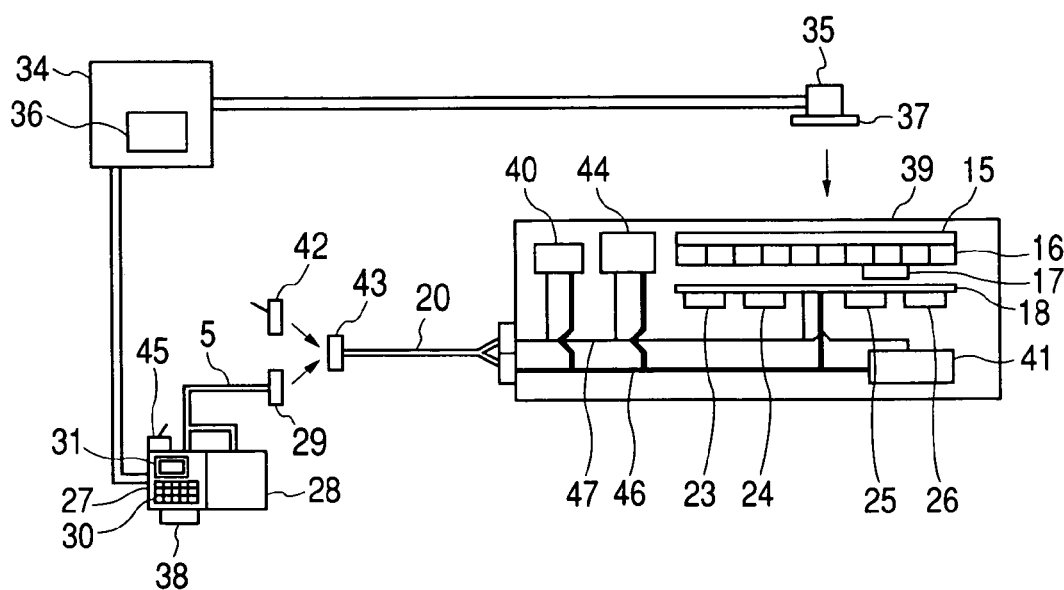
FIG. 5 shows connection of an electronic cassette and a wireless communication unit.

FIG. 5 is a diagram showing the structure of a fifth embodiment, in which the interior of an electronic cassette 39 is illustrated. In FIG. 5, the parts same as those in the previously mentioned drawings are designated by the same reference characters.

In this embodiment, an image memory 40 and a battery 41 are additionally provided in the interior of the electronic cassette 39 as components different from those in the electronic cassette 14 show in FIG. 4. In addition, a wireless communication module 42, a connector 43 that can be connected with a connector 29 and a control portion 44 for controlling the communication scheme and operations of the electronic cassette 39 are provided. The system control portion 27 is additionally provided with a wireless communication terminal 45 for communicating with the wireless communication module 42. With the provision of the image memory 40, the battery 41 and the wireless communication module 42, the operator can use the electronic cassette 39 on the cableless basis (i.e. without a cable). In the following, the operations of the components will be described.

In the state shown in FIG. 5, nothing is connected to the connector 43 of the electronic cassette 39. Under this state, the control portion 44 suspends power supply to each component of the sensor from the battery 41 in accordance with the unconnected state of the connector 43. The system control portion 27 detects that the connection has not been established based on absence of communication with the control portion 44 of the electronic cassette 39 and sends a command to a monitor 31 for displaying input information from interface 30 and image data, to cause the monitor 31 to display a content indicating the disconnected state.

In the case that the electronic cassette 39 is to be used without the cable, the operator connects the wireless communication module 42 with the connector 43. Then, in response to the connection of the wireless communication module 42, the control portion 44 sends a command to cause the battery 41 to supply power to the wireless communication module 42. Thus, the wireless communication module 42 is supplied with power from the electric energy stored in the battery 41 in advance so as to be in an operable state. At that time, the battery 41 supplies only the power required for the operations of the components of wireless communication module 42. In other words, power has not been supplied to each components of the sensor via a power supply cable 46 yet. The control portion 44 informs the wireless communication terminal 45 of the fact that wireless communication module 42 has been connected with the electronic cassette 39, through the wireless communication module 42. Based on that information from the wireless communication terminal 45, the system control portion 27 sends a command to the monitor 31 to cause it to display a content indicating that the electronic cassette 14 is in an operable state on the cableless basis.

Next, the operator enters through the interface 30 an imaging start command for the system control portion 27 in order to perform the imaging operation. Upon receiving the command, the system control portion 27 transmits a start command to the control portion 44 via the wireless communication terminal 45 and the wireless communication module 42. Upon receiving the command, the control portion 44 commands the battery 41 so that power required for driving of the components of the sensor is supplied from the battery 41 via the power supply cable 46. At the same time, the control portion 44 transmits an imaging command signal to the electric circuit board 18 via a signal cable 47. In addition, the system control portion 27 drives the X-ray tube 35 of the portable X-ray generating apparatus 34 by means of the high voltage generating power source 36, drives an X-ray stop 37 to set an irradiation field, and causes an X-ray beam to be radiated. The drive circuit 23 on the electric circuit board 18 detects an X-ray exposure termination signal from an X-ray exposure dose monitor 17, high voltage power application from the high voltage generating power source 36 or an X-ray tube current signal to drive TFT switches so as to read out electric charges in the manner same as the embodiment shown in FIG. 4. In the scintillator 15, the base material of the phosphor is exited by high energy X-rays and fluorescence within the visible light range is generated by recombination energy released upon recombination. The photo detector array 16 converts light generated in the scintillator 15 into an electric signal.

The X-ray exposure dose monitor 17 detects the radiated X-rays to transmit information obtained by the detection to the control portion 44. The control portion 44 further transmits the information to the system control portion 27 via the wireless communication module 42 and the wireless communication terminal 45. The system control portion 27 drives the high voltage generating power source 36 to stop or adjust the X-rays based on that information. The drive circuit 23 drives the photo detector array 16 under a control of the control portion 44 to read out a signal from each pixel. Matrices in the sensor are subjected to selection by the drive circuit 23 and digital image data obtained through the amplifier 24, the A/D conversion circuit 25 and the serializing circuit 26 is stored in the image memory 40. In addition, the control portion 44 transmits the obtained digital image data to the system control portion 27 via the wireless communication module 42 and the wireless communication terminal 45, so that the digital image data is stored in the recording apparatus 38. Since the data amount of the image data is large, it is desirable that the frequency of the communication wave be in a band of several gigahertz in order to realize communication within a short time. The image data stored in the image memory 40 is temporally data until the image data is stored in the recording apparatus 38, and therefore the control portion 44 controls to delete the image data stored in the image memory 40 when informed by the system control portion 27 of completion of the storing of the data in the recording apparatus 38. At the same time, the control portion 44 commands the battery 41 to stop the power supply to the components of the sensor. The filing of the digital image data stored in the recording apparatus 38 is performed in the manner same as that described in connection with the prior art.

While in this embodiment the wireless communication uses a frequency band of several gigahertz, the wireless communication module may be replaced with an optical communication module such as an infrared communication module.

As per the above, in the case that the electronic cassette is used without a cable, troublesome handling of the cable can be eliminated, since the operation of connecting a cable is not necessary. However, since power consumption required for the imaging operation with the electronic cassette is large, it is necessary to increase the capacity of the battery when successive imaging operations are to be enabled. An increase in the capacity leads to an increase in the volume and the weight of the battery such as a lithium ion battery. This may deteriorate operationality of the electronic cassette, which is required to be portable and lightweight.

In view of the above situation, in the embodiment shown in FIG. 5, the connector 43 of the electronic cassette 39 side is adapted to be connectable with the connector 29 of the system control portion 27 side. When the connector 29 and the connector 43 are connected, the system control portion 27 and the control portion 44 perform communication and power supply related to the above-described operations of the electronic cassette 39 through the cables 5 and 20 and the connectors 29 and 43. In response to the connection of the connectors 29 and 43, the control portion 44 switches the communication path and the power supply path to the cable basis. At that time, power is not supplied from the power source portion 28 to the sensor side, but charging of the battery may be performed if the battery has not been charged up to its full capacity. The control portion 44 informs the system control portion 27 of the fact that electronic cassette 39 is connected with the cable. Upon receiving that information, the system control portion 27 sends a command to the monitor 31 to cause the monitor to display a content indicating that the electronic cassette is in an operable state on the cable basis. Next, the operator enters through the interface 30 an imaging start command for the system control portion 27 in order to perform the imaging operation. Upon receiving the command, the system control portion 27 transmits a start command to the control portion 44. At the same time, the system control portion 27 causes the power source portion 28 to supply power required for driving the components of the sensor of the electronic cassette 39. On the other hand, the control portion 44 transmits an imaging command signal to the electric circuit board 18 via the signal cable 47. The system control portion 27 sends the command same as that described before to the portable X-ray generating apparatus 34 so as to cause an X-ray beam to be radiated. In addition, the system control portion 27 and the control portion 44 perform the series of communications same as those described before on the cable basis, so that the obtained image data is stored in the recording apparatus 38. Then, the system control portion 27 commands the power source portion 28 to stop the power supply to the components of the sensor.

As per the above, imaging may be performed with a cable in the case that many imaging operations are to be performed successively, and therefore imaging can be performed without deteriorating portability of the electronic cassette. While in this embodiment the wireless communication module is constructed as a detachable module, the wireless module may be accommodated in the electronic cassette in the case the cassette is used in most cases for a small number of times of imaging on the cableless basis.

As has been described in the foregoing, the X-ray imaging apparatus according to the present invention has a connecting portion for connection with an external apparatus provided at a position within a prescribed distance range from the body of the electronic cassette. With this feature, it can be connected with the external apparatus easily irrespective of the size of the electronic cassette or the body type of the patient. In addition, with the provision of indication of the connection state at the connecting portion, whether attachment/detachment is allowed or not can be easily recognized. Furthermore, with the provision of the wireless communication module at the connecting portion, communication means can be selected in accordance with the state of use of the electronic cassette.

[Other Embodiment]

Note that the present invention may be applied to either a system constituted by a plurality of apparatuses (e.g. an image processing apparatuses, interfaces, radiographic apparatuses, X-ray generation apparatuses, and the like) or an arrangement that integrates an image processing apparatus and a radiographic apparatus, or the like.

The present invention is not limited to the above embodiments and carious changes and modifications can be made within the sprit and scope of the present invention. Therefore to apprise the public of the scope of the present invention, the following claims are made.

What is claimed is:

1. An X-ray imaging apparatus comprising:
  a sensor for converting radiation into an electric signal;
  an electronic cassette for accommodating said sensor;
  a first cable connected to a side surface of said electronic cassette; and
  a first connector provided at an end of said first cable;
  a second connector to be connected to said first connector;
  a second cable connected to said second connector; and
  an external apparatus connected to said second cable for transmitting/receiving an electric signal to/from said electronic cassette and/or supplying electric power to said cassette via said first and second cables,
  wherein said electronic cassette is provided with a wireless communication unit capable of communicating with said external apparatus, said wireless communication unit being connectable to said first connector, and said electronic cassette is provided with a battery for supplying electric power and a control unit for controlling said wireless communication unit and controlling power supply from said battery, wherein when said wireless communication unit is connected to said first connector, said control unit controls to cause said battery to supply electric power to said wireless communication unit.

2. An X-ray imaging apparatus according to claim 1, wherein when said wireless communication unit receives an imaging start signal, said control unit controls to cause said battery to supply electric power to said sensor.

* * * * *

UNITED STATES PATENT AND TRADEMARK OFFICE
CERTIFICATE OF CORRECTION

PATENT NO. : 7,015,478 B2  Page 1 of 1
APPLICATION NO. : 10/715723
DATED : March 21, 2006
INVENTOR(S) : Yamamoto It is certified that error appears in the above-identified patent and that said Letters Patent is hereby corrected as shown below:

On the Title page
    Under Item (22), "Filed:"
        please change "Nov. 14, 2003" to --Nov. 17, 2003--.

Signed and Sealed this

Twelfth Day of September, 2006

JON W. DUDAS
*Director of the United States Patent and Trademark Office*